United States Patent
Tornier

(10) Patent No.: US 7,033,396 B2
(45) Date of Patent: Apr. 25, 2006

(54) SHOULDER OR HIP PROSTHESIS FACILITATING ABDUCTION

(75) Inventor: Alain Tornier, Saint-Ismier (FR)

(73) Assignee: Tornier, Saint-Ismier (FR)

( * ) Notice: Subject to any disclaimer, the term of this patent is extended or adjusted under 35 U.S.C. 154(b) by 0 days.

(21) Appl. No.: 10/612,296

(22) Filed: Jul. 3, 2003

(65) Prior Publication Data

US 2004/0039449 A1    Feb. 26, 2004

(30) Foreign Application Priority Data

Jul. 5, 2002    (FR)    ..................................    02 08500

(51) Int. Cl.
*A61F 2/40*    (2006.01)
(52) U.S. Cl. .................................................. 623/19.11
(58) Field of Classification Search .. 623/19.11–19.14, 623/20.35, 20.36, 22.11–22.19, 23.4
See application file for complete search history.

(56) References Cited

U.S. PATENT DOCUMENTS

| | | | |
|---|---|---|---|
| 3,916,451 A | | 11/1975 | Buechel et al. |
| 4,846,840 A | * | 7/1989 | Leclercq et al. .......... 623/22.15 |
| 5,702,457 A | * | 12/1997 | Walch et al. ............ 623/19.13 |
| 5,723,018 A | * | 3/1998 | Cyprien et al. .......... 623/19.13 |
| 5,741,335 A | | 4/1998 | Gerber et al. |
| 5,928,285 A | * | 7/1999 | Bigliani et al. .......... 623/19.13 |
| 6,203,575 B1 | | 3/2001 | Farey |
| 6,749,637 B1 | * | 6/2004 | Bahler ...................... 623/19.14 |
| 6,761,740 B1 | * | 7/2004 | Tornier .................... 623/19.13 |
| 6,790,234 B1 | * | 9/2004 | Frankle ................... 623/19.12 |
| 2002/0143402 A1 | * | 10/2002 | Steinberg ................. 623/22.16 |
| 2003/0097183 A1 | * | 5/2003 | Rauscher et al. ........ 623/19.13 |
| 2003/0114933 A1 | * | 6/2003 | Bouttens et al. ......... 623/19.13 |
| 2004/0002765 A1 | * | 1/2004 | Maroney et al. ......... 623/19.12 |
| 2004/0030394 A1 | * | 2/2004 | Horber .................... 623/18.11 |

FOREIGN PATENT DOCUMENTS

EP    0524857    1/1993

* cited by examiner

*Primary Examiner*—Alvin J. Stewart
(74) *Attorney, Agent, or Firm*—Dowell & Dowell, P.C.

(57) ABSTRACT

The prosthesis of this invention comprises a humeral or femoral component presenting a concave articulation surface, and an intermediate component presenting first and second convex articulation surfaces intended to cooperate respectively with said concave articulation surface of the humeral or femoral component and with a concave glenoid or cotyloid articulation surface. The locus of the instantaneous centers of rotation of the first convex articulation surface, with respect to the concave humeral or femoral articulation surface, and the locus of the instantaneous centers of rotation of the second convex articulation surface on the glenoid or cotyloid surface, are located on either side of the first surface.

13 Claims, 8 Drawing Sheets

SHOULDER OR HIP PROSTHESIS FACILITATING ABDUCTION

BACKGROUND OF THE INVENTION

1. Field of the Invention

The present invention relates to a complete or partial shoulder or hip prosthesis making it possible to reproduce, with an improved degree of precision, the characteristics of a natural joint.

2. Description of the Related Art

In the domain of shoulder prostheses, it is known, for example from European Patent Application 0 299 889, to create a convex articular surface on a glenoid component, while a concave articular surface of corresponding shape is formed on a humeral component. The glenoid component of such a surface is very invasive and a subacromial conflict of the humeral component may occur at the end of a movement of abduction.

Furthermore, U.S. Pat. No. 4,846,840 discloses producing, on an intermediate element of a prosthesis, two substantially concentric convex surfaces with a view to their articulation on concave surfaces of corresponding shapes, provided respectively on two bones to be articulated on each other. Such a prosthesis is unstable, particularly due to the offset between the two sets of articular surfaces provided in this prosthesis.

It is a more particular object of the invention to overcome these drawbacks by proposing a shoulder or hip joint prosthesis reproducing the anatomical articulation, while facilitating the abduction of the arm or the leg, in the absence of the cover of the rotators for the shoulder or of the stabilizing structures of the hip, thanks to an increase of the lever arm of the effort exerted by the deltoid muscle or the gluteus medius muscle at the beginning of abduction.

SUMMARY OF THE INVENTION

In this spirit, the invention relates to a shoulder or hip prosthesis which comprises a humeral or femoral component presenting a concave articulation surface and an intermediate component presenting first and second convex articulation surfaces, intended to cooperate respectively with the concave articulation surface of the humeral or femoral component and with a concave glenoid or cotyloid articulation surface, natural or belonging to a glenoid or cotyloid component. This prosthesis is characterized in that the locus of the instantaneous centres of rotation of the first convex articulation surface with respect to the concave humeral or femoral articulation surface, and the locus of the instantaneous centres of rotation of the second convex articulation surface on the glenoid or cotyloid articulation surface, lie on either side of the first convex surface.

Thanks to the invention, in the case of a shoulder prosthesis, the lever arm of the deltoid muscle exerting the effort of abduction of the humerus on the shoulder is great, which facilitates the abduction thanks to a slide of the concave humeral articulation surface with respect to the first convex articulation surface of the intermediate element. In the case of a hip prosthesis, the abduction of the femur, which is controlled by the gluteus medius muscle, is facilitated.

According to advantageous aspects of the invention, this prosthesis incorporates one or more of the characteristics of Claims 2 to 12.

BRIEF DESCRIPTION OF THE DRAWINGS

The invention will be more readily understood and other advantages thereof will appear more clearly in the light of the following description of four forms of embodiment of a prosthesis in accordance with its principle, given solely by way of example and made with reference to the accompanying drawings, in which.

DESCRIPTION OF PREFERRED EMBODIMENTS

Figure 1:
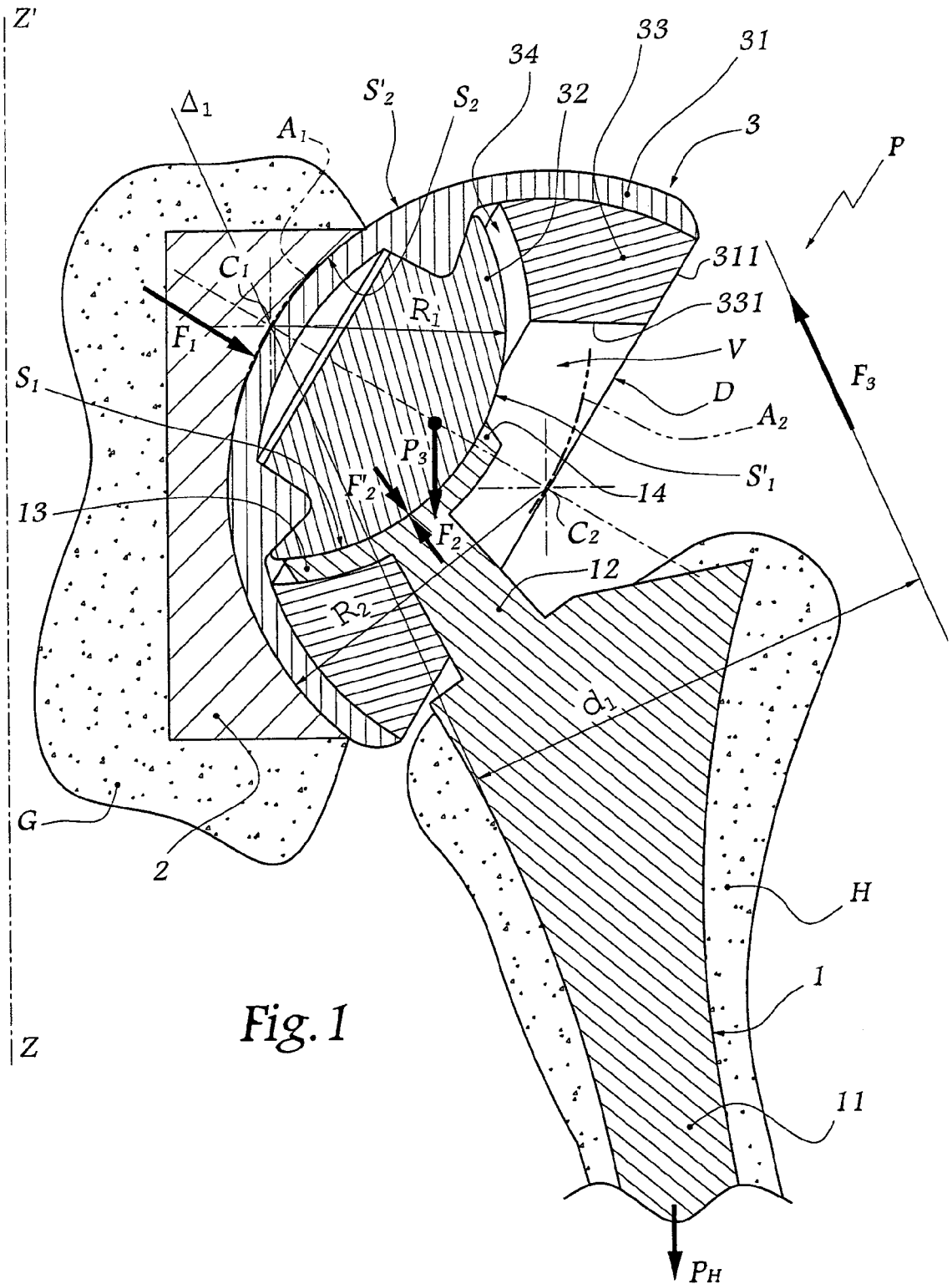
FIG. 1 is a sagittal section of a shoulder prosthesis according to the invention in place on a patient, while the patient's arm is in lower position.

Referring now to the drawings, the prosthesis P shown in FIGS. 1 to 5 comprises a humeral component 1 which includes a part 11 intended to be anchored in the medullary cavity of the humerus H of the articulation to be equipped with the prosthesis P. Part 11 extends by a stem 12 projecting outside the humerus once the latter is resectioned and at the end of which is formed a plate 13 in one piece with parts 11 and 12. This plate might equally well be connected on parts 11 and 12.

The plate 13 defines a concave surface $S_1$ of which the concavity faces towards the glenoid cavity G of the shoulder.

The prosthesis also comprises a glenoid component 2 anchored in the glenoid cavity of the shoulder and defining a concave surface $S_2$ whose concavity faces towards the outside of the glenoid cavity.

Between the components 1 and 2 there is interposed an intermediate component 3 forming a hollow dish 31 inside which are immobilized a button 32 and a washer 33.

The elements 32 and 33 are fixed by any appropriate means inside the dish 31, for example by screwing, interlocking and/or adhesion. In a variant, the button 32 may be in one piece with the dish 31.

$S'_1$ denotes the convex surface of the button 32 accessible from outside the dish 31.

The surfaces $S_1$ and $S'_1$ are both portions of sphere having substantially the same radius $R_1$, with the result that the plate 13 can slide over the surface $S'_1$ of the button 32.

The convex outer surface $S'_2$ of the dish 31 is also in the form of portions of sphere, with a radius $R_2$ similar to the radius of the surface $S_2$, this allowing a relative sliding movement of the surfaces $S_2$ and $S'_2$.

The elements 32 and 33 are housed in an internal volume V of the dish 31, this volume being defined inside the surface $S'_2$ and an imaginary disc D in abutment on the peripheral edge 311 of the dish 31. According to a variant of the invention (not shown), the washer 33 may project out of the volume V.

The plate 13 is in the form of a dish and extends around the stem 12, forming a circular peripheral extension or projection 14 which may be engaged in a peripheral notch 34 made, in the volume V, between the button 32 and the washer 33.

The washer 33 comprises an internal truncated surface 331 against which the stem 12 may come into abutment, with the result that the surface 331 constitutes a stop for the movement of slide of the plate 13 with respect to the button 32. The surface 331 is not necessarily truncated.

Z–Z' denotes a vertical axis substantially parallel to the spine of the patient when standing.

The component 3 is subjected to the weight $P_3$, as well as to an effort $F_1$ which is transmitted thereto by the glenoid cavity. This assembly is also subjected to an effort of reaction $F_2$ coming from the plate 13. The efforts $P_3$, $F_1$ and $F_2$ are balanced in position of rest of the humerus H.

The component 1 is subjected to its weight cumulated with that of the humerus, weight of which $P_H$ denotes the resultant. The component 1 is also subjected to the reaction of the button 32, i.e. to an effort $F'_2$ opposite the effort $F_2$. Finally, the component 1 is subjected to an effort $F_3$ exerted by the deltoid muscle supporting the humerus H.

The instantaneous centre $C_1$ of rotation of the surface $S_1$ with respect to the surface $S'_1$ is a centre common to the spheres defining the surfaces $S_1$ and $S'_1$. Taking into account the geometry of the component 3, this centre $C_1$ is located in the glenoid cavity G, i.e. in a medial position with respect to the anatomical centre of rotation of the shoulder before operation.

In practice, the radius of curvature $R_1$ of the surfaces $S_1$ and $S'_1$ is chosen to be as great as possible, with the result that the centre $C_1$ is as medial as possible. The position of the button 32 in the dish 31 is also chosen to that end.

Furthermore, the instantaneous centre of rotation $C_2$ between the surfaces $S'_2$ and $S_2$ is the common centre of the spheres containing these surfaces and it lies beyond the surface $S'_1$ with respect to the surface $S_2$. In practice, the centre $C_2$ is substantially close to the anatomical centre of rotation of the shoulder before operation. The spatial relation between the centres $C_1$ and $C_2$ is therefore an image of the spatial relation between the centre $C_1$ and the anatomical centre of rotation with respect to which the muscles and the ligaments of the shoulder are implanted.

This positioning of the centres $C_1$ and $C_2$ makes it possible to facilitate the movement of abduction of the humerus H, without necessitating that the effort $F_3$ exerted by the deltoid muscle on that occasion be too great.

Figure 2:
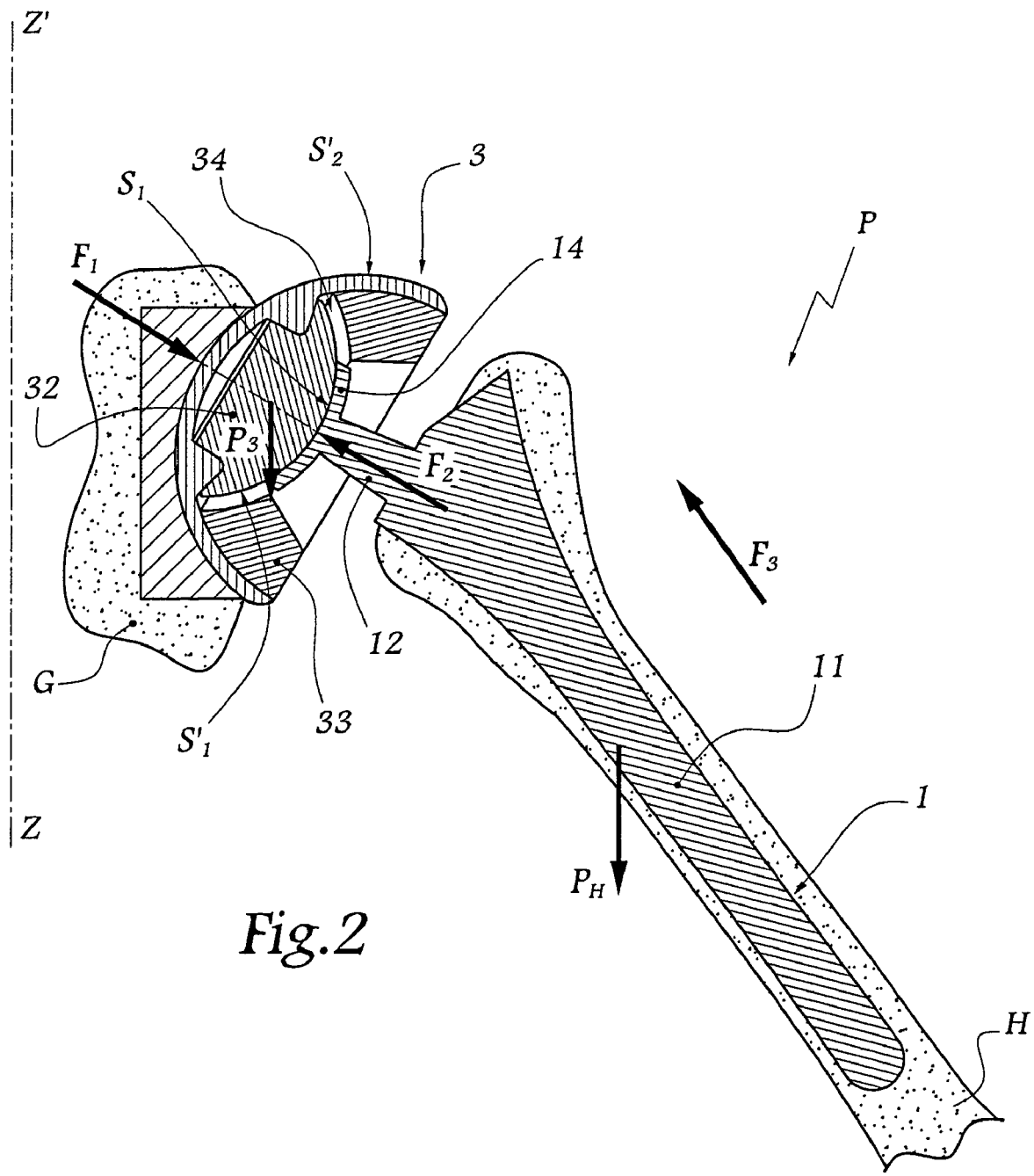
FIG. 2 is a section similar to FIG. 1 during a first phase of the movement of abduction of the humerus.

In effect, during a first step of abduction represented by the passage from the configuration of FIG. 1 to that of FIG. 2, the effort $F_3$ exerted by the deltoid muscle is exerted at a first, relatively large distance $d_1$ from a straight line $\Delta_1$ parallel to the effort $F_3$ and passing through the centre $C_1$. This distance $d_1$ represents the lever arm of the effort $F_3$ with respect to the instantaneous centre of rotation $C_1$, this relatively great lever arm making it possible to generate, relatively easily, a movement of slide of the plate 13 on the button 32, while the dish 31 remains immobile with respect to the component 2. During this first phase of abduction, the forces of reaction $F_1$ and $F_2$ between the glenoid cavity and the component 3 maintain approximately the same direction, hence the dish 31 is maintained in equilibrium.

Figure 3:
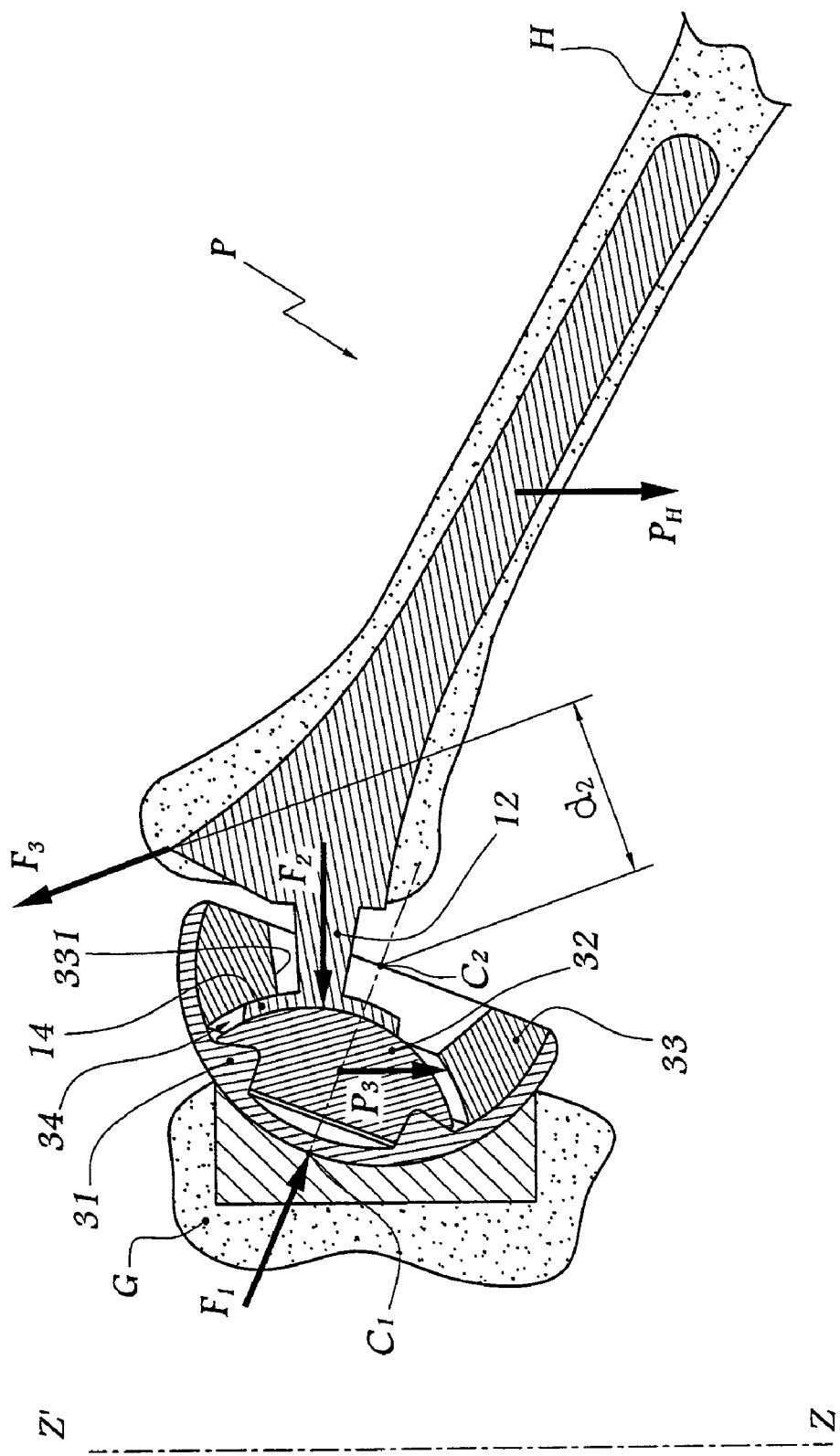
FIG. 3 is a section similar to FIG. 1 during a second phase of the movement of abduction.
Figure 4:
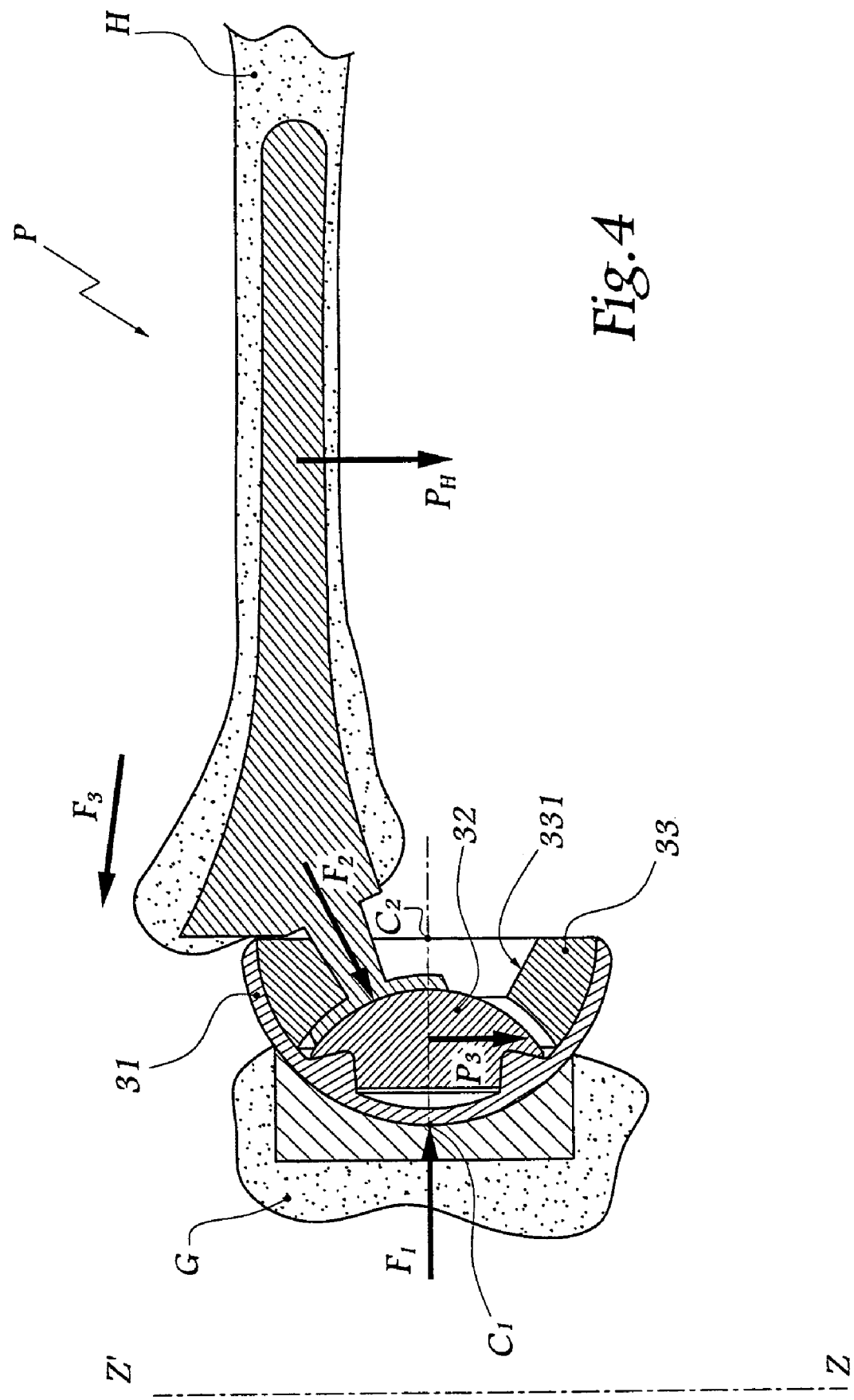
FIG. 4 is a section similar to FIG. 1 at the end of the movement of abduction.

If the movement of abduction is prolonged until the configuration of FIG. 3 is attained, the plate 13 continues to slide on the surface $S'_1$ of the intermediate component 3, while the dish 31 starts a movement of slide against the surface $S_2$ of the component 2. In effect, during this additional movement corresponding to the passage from the configuration of FIG. 2 to that of FIG. 3, the efforts $F_1$ and $F_2$ change direction.

If the movement of abduction is continued up to a maximum opening corresponding substantially to a horizontal position of the humerus, the stem 12 may come into abutment against the surface 331 of the washer 33 at the level of its upper part and the movement of articulation then occurs solely by a displacement of the dish 31 with respect to the component 2. In practice, the essential function of the washer 33 is to avoid a metal/metal contact between the plate 11 or the stem 12 and the dish 31.

In this way, the instantaneous centre of rotation of the articulation no longer lies in the glenoid cavity, like $C_1$, but inside the humerus, in a position closer to that of the anatomical centre of rotation. In this posture, the value of the lever arm $d_2$ between the effort $F_3$ exerted by the deltoid muscle and the centre $C_2$ is of the same order of magnitude as the value of $d_1$.

In practice, the centre $C_1$ describes, during the movement of abduction, an arc of circle $A_1$ virtually merged in the Figures with the trace of the surfaces $S_2$ and $S'_2$ as the radii $R_1$ and $R_2$ are such that the centre $C_1$ lies virtually at the level of these surfaces. This arc of circle $A_1$ is the locus of these instantaneous centres of rotation in the course of the movement of abduction. The centre $C_2$ describes an arc of circle $A_2$ which constitutes the locus of the centres of rotation between the surfaces $S'_2$ and $S_2$.

The locus $A_1$ of the centres of rotation $C_1$ is not necessarily merged with the trace of the surfaces $S_2$ and $S'_2$, this configuration following simply from the version shown in the Figures. In practice, the locus $A_1$ is as medial as possible and, for example, located in the component 2 or in the glenoid cavity G, in order to increase the lever arm of the deltoid muscle.

Figure 5:
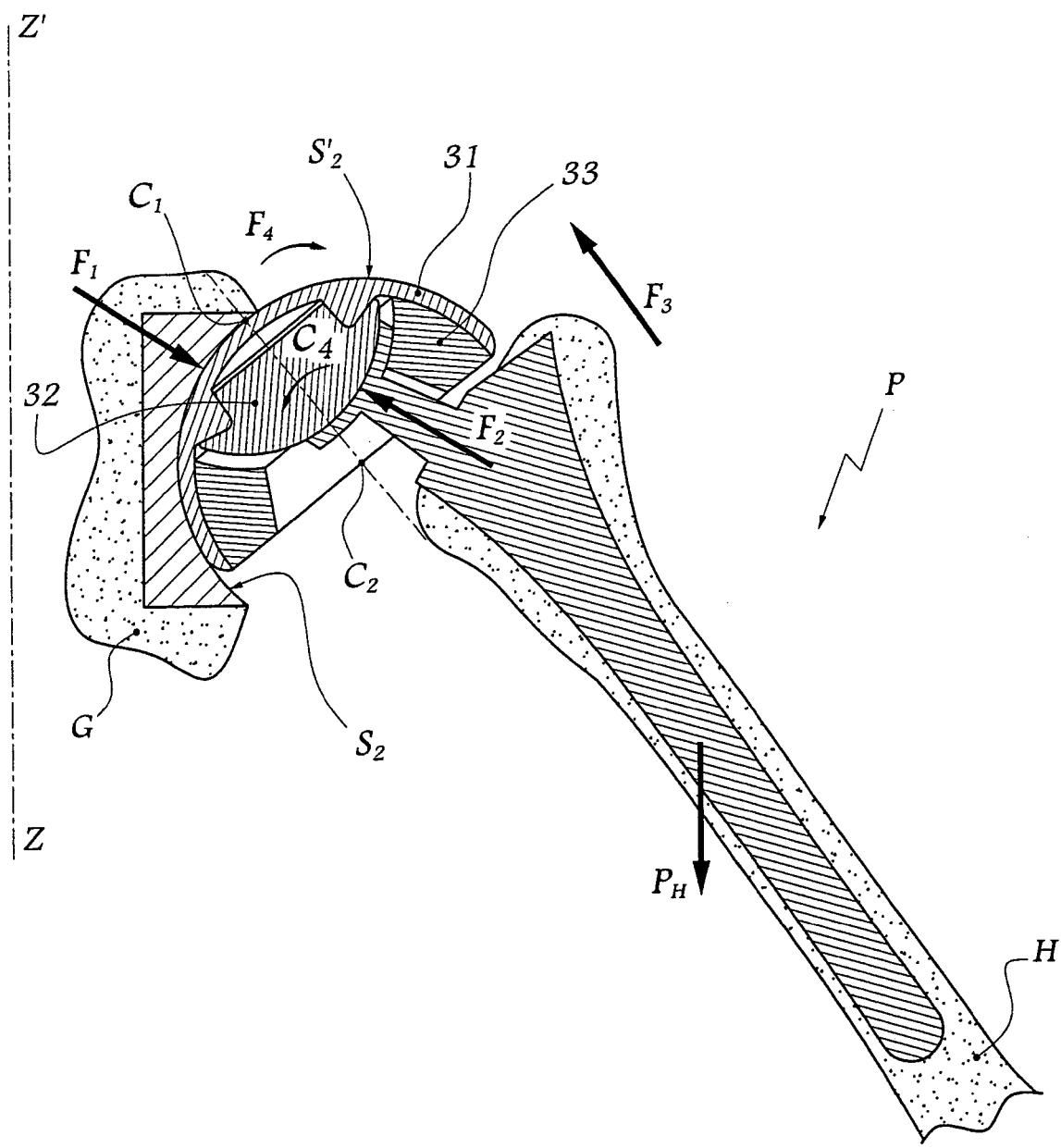
FIG. 5 is a section similar to FIG. 1 when the prosthesis is subjected to an effort tending to move it away from its position of equilibrium.

As is more particularly visible in FIG. 5, the prosthesis according to the invention presents a considerable dynamic stability. In effect, if, from the position of FIG. 2 and under identical load conditions, the dish 31 is displaced in the direction of arrow $F_4$, there is created, due to the offset of the efforts $F_1$ and $F_2$, a return couple $C_4$ which tends to return the component 3 in a direction opposite the displacement $F_4$, thus creating the conditions of a stable equilibrium of the component 3.

Figure 6:
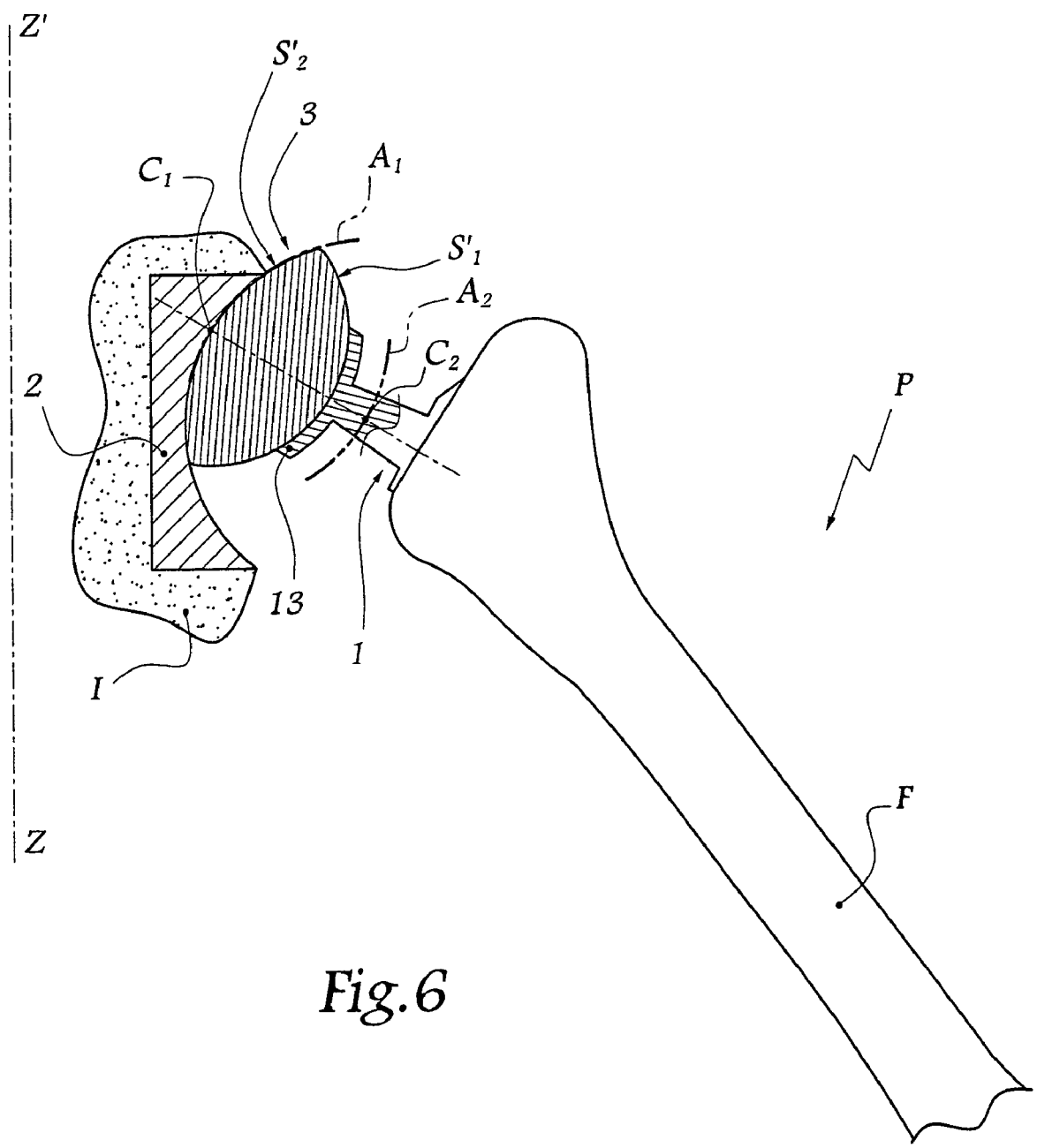
FIG. 6 is a section similar to FIG. 1, on a smaller scale and with the femur shown in outside view, for a hip prosthesis in accordance with a second form of embodiment of the invention.

In the second form of embodiment of the invention shown in FIG. 6, the components 1 and 2 are respectively intended to be anchored in the femur F and the hip bone I. They are similar to those described with reference to the first embodiment. The intermediate component 3 differs from the preceding one in that it has a substantially bi-convex shape with a first surface $S'_2$ in the form of portions of sphere of which $C_1$ denotes the geometrical centre and a second surface $S'_2$, likewise in the form of portions of sphere, of which $C_2$ denotes the geometrical centre. The centres $C_1$ and $C_2$ are the instantaneous centres of rotation during the movements of slide of the plate 13 of the component 1 with respect to the component 3 and of the component 3 with respect to the component 2.

In practice, forces of friction (not shown) must be overcome during the movements of the humerus H or of the femur F. These forces have low values with respect to the efforts mentioned above, which makes it possible to disregard the forces of friction in the foregoing explanations.

In addition to the facility of the movement of abduction that it allows, the prosthesis according to the invention presents the particular advantage that the interventions to be made on the glenoid cavity or on the hip bone for the implantation of the component 2 are limited, and even nil. In effect, the prosthesis according to the invention does not necessarily comprise a glenoid or cotyloid component since the glenoid or cotyloid articular surface may be conserved if its state is good. In the case of a complete prosthesis as shown in the accompanying Figures, the component 2 has a small volume, unlike the corresponding components of the majority of prior art prostheses.

Figure 7:
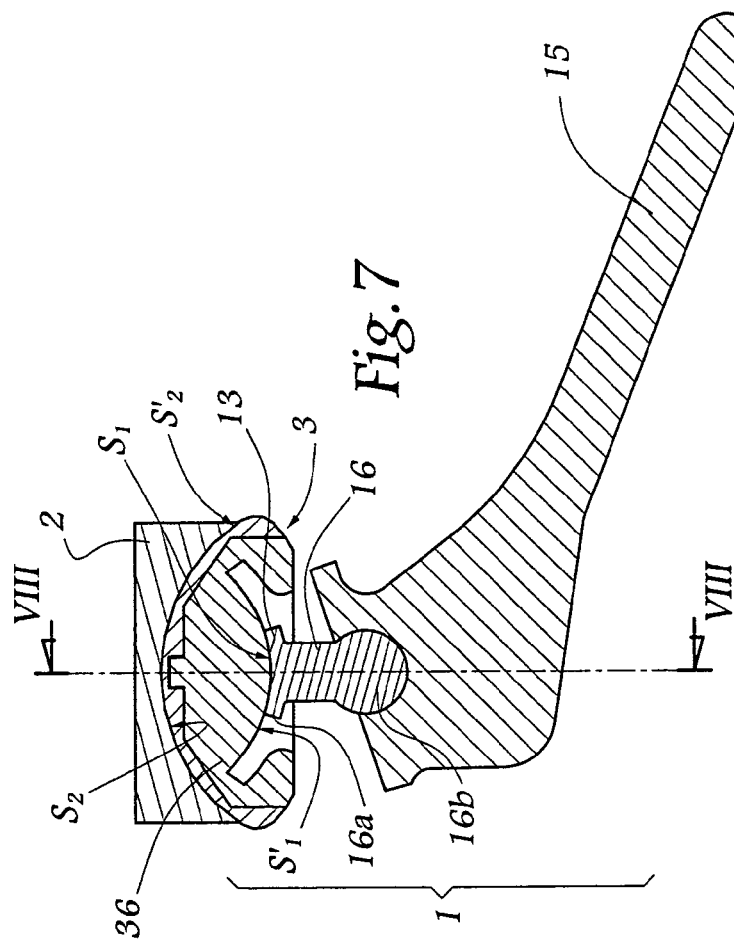
FIG. 7 is a longitudinal section of a shoulder prosthesis in accordance with a third form of embodiment of the invention.
Figure 9:
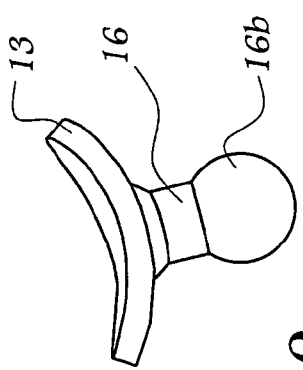
FIG. 9 is a view in perspective of a part of the humeral component of the prosthesis of FIGS. 7 and 8.
Figure 8:
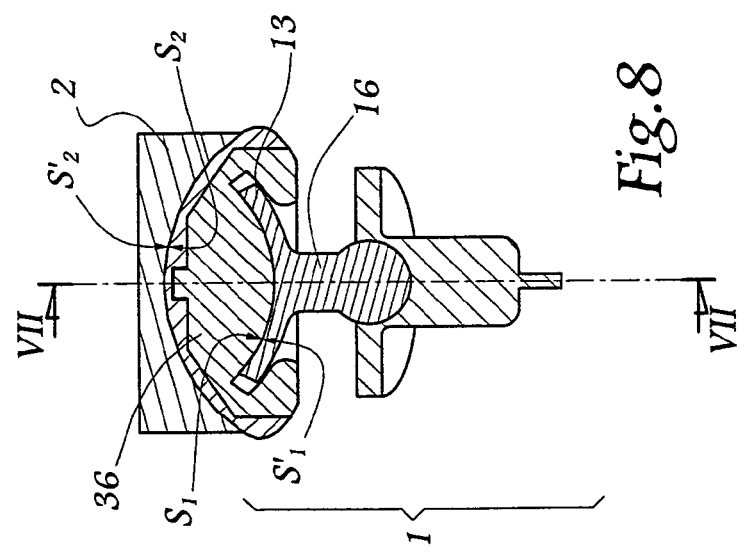
FIG. 8 is a section along line VIII—VIII of FIG. 7, VII—VII indicating the plane of section of FIG. 7.

In the third form of embodiment of the invention shown in FIGS. 7 to 9, the components 1 and 2 are respectively intended to be anchored in the humerus and in the glenoid cavity. The intermediate component 3 defines two convex articular surfaces $S'_1$ and $S'_2$ intended to cooperate respectively with concave articular surfaces $S_1$ and $S_2$ formed by the components 1 and 2.

The loci of the instantaneous centres of rotation of the surfaces $S'_1$ and $S'_2$ on the surfaces $S_1$ and $S_2$ are, as previously, located on either side of the surface $S'_1$.

This embodiment differs from the preceding ones in that the humeral component 1 is not in one piece but in two parts. More precisely, it comprises a humeral stem 15 and a finger 16 of which one end 16a forms the plate 13, while its other end is of substantially spherical shape and received in a cavity of corresponding shape in the stem 15.

The plate 13 is substantially oval in shape, with its smallest dimension in the plane of FIG. 7, which makes it possible to improve the amplitude of the movement of abduction.

As is visible in FIG. 8, the amplitude of the movement transverse to the sagittal plane is limited.

The width of the plate 13 in the plane of FIG. 8 avoids an untimely separation of the elements 1 and 3.

It will be noted that one sole one-piece element 36 performs the role of the button 32 and of the washer 33 of the first embodiment.

Figure 10:
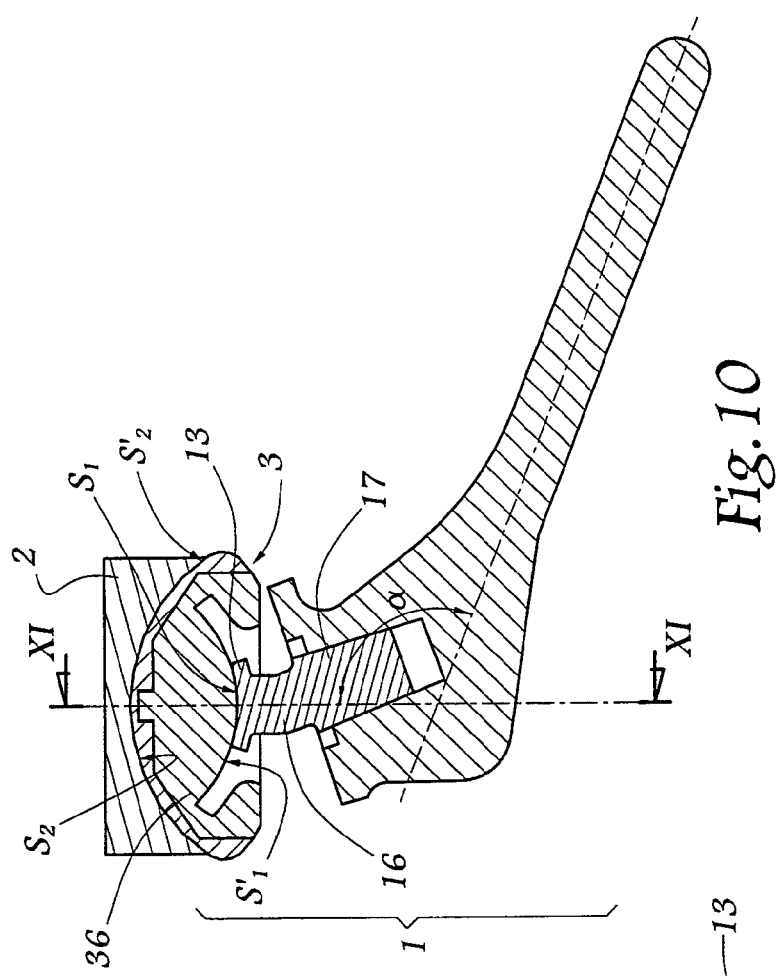
FIG. 10 is a view similar to FIG. 7 for a hip prosthesis in accordance with a fourth form of embodiment of the invention.
Figure 11:
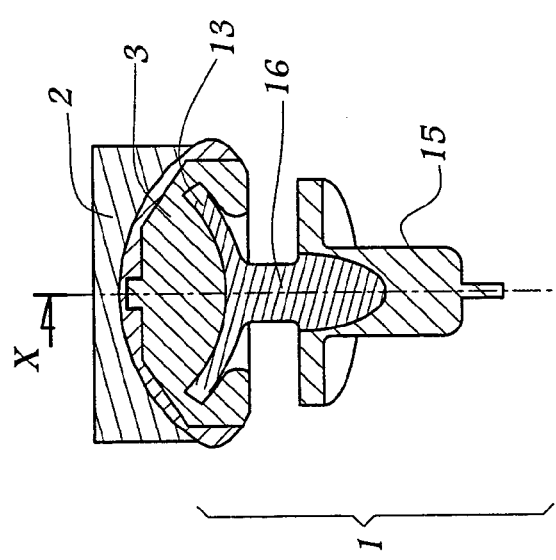
FIG. 11 is a section along line XI—XI of FIG. 10, X—X indicating the plane of section of FIG. 10.
Figure 12:
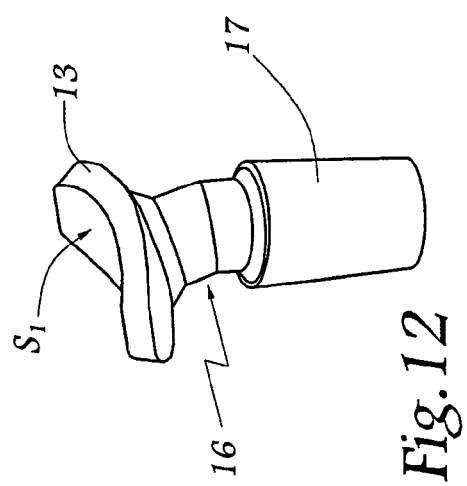
FIG. 12 is a view in perspective of a part of the femoral component of the prosthesis of FIG. 10.

In the fourth form of embodiment of the invention shown in FIGS. 10 and 11, the components 1 and 2 are respectively intended to be anchored in the femur and in the hip bone. The intermediate component 3 is similar to that of the third embodiment and the convex surfaces $S'_1$ and $S'_2$ that it defines induce the same positioning of their instantaneous centres of rotation as previously.

This embodiment differs from the preceding one in that the assembly between the femoral stem 15 and the finger 16 is conical. A truncated part 17 is provided on the finger 16 in order to be engaged in a housing in the stem 15.

In addition, the plate 13 which defines the concave surface SI intended to cooperate with the surface $S'_1$ of the component 3 is of substantially rectangular shape. As in the third embodiment, the smallest dimension of the plate 13 is disposed in the plane of FIG. 10.

It will be noted that the finger 16 is not rectilinear, which makes it possible to optimize the position of the centre of rotation of the plate 13. In practice, the angle α between the axis transverse to the surface $S_1$ and the longitudinal axis of the stem 15 is chosen to be equal to about 130°, which presents a good compromise between the necessity of obtaining a maximum amplitude of the movement of abduction and the wish to reduce the risk of dislocation.

According to an aspect of the invention which has not been shown, the neck joining parts 13 and 17 of the finger 16 may equally well be bent, in the sagittal plane, in a direction opposite that shown. This neck may also be bent in a plane perpendicular to the sagittal plane, which makes it possible to vary the anteversion.

Assembling between the elements 15 and 16 may be reversible. In other words, the finger 16 may possibly be dismounted from the stem 15. This reversible nature of the assembling of the elements 15 and 16 may also be envisaged for the third embodiment.

The invention has been represented with articular surfaces in the form of portions of spheres. However, it is applicable to other types of surfaces, for example cylindrical with circular or paraboloidal base, in which case the position of the instantaneous centres of rotation may vary during the movement of abduction on loci which are not necessarily arcs of circle. In the same way, it may be conceived that the surfaces $S_1$ and $S'_1$ be cylindrical, with rectilinear generatrix and with circular base, with a substantially antero-posterior axis allowing only the movement of abduction, while the surfaces $S_2$ and $S'_2$ would remain spherical, allowing both the movement of abduction and the axial-humeral or axial-femoral rotation.

In the accompanying Figures, the lengths of the arrows are indicative and must not be considered as strictly representative of the intensities of the corresponding efforts. The same applies to their orientation.

The invention has been represented during its use with complete shoulder and hip prostheses. However, it is applicable with a prosthesis not having a glenoid component, the concave articular surface of the glenoid cavity being used instead of the surface $S_2$ shown in the Figures. The same applies to a hip prosthesis where the natural cotyloid cavity can be used. The characteristics of the different forms of embodiment shown may be combined together within the framework of the present invention. In particular, the prostheses of the second and fourth embodiments might be adapted to the shoulder, while those of the first and third embodiments might be adapted to the hip.

What is claimed is:

1. A shoulder or hip prosthesis comprising a humeral or femoral component having a concave articulation surface $(S_1)$ and an intermediate component having first and second convex articulation surfaces $(S'_1)$ $(S'_2)$, intended to cooperatively slide when the prosthesis is in use, respectively, against said concave articulation surface of said humeral or femoral component and against a concave glenoid or cotyloid articulation surface $(S_2)$, natural or belonging to a glenoid or cotyloid component, wherein a locus of instantaneous centers of rotation $(C_1)$ of said first convex articulation surface $(S'_1)$ with respect to the concave humeral or femoral articulation surface $(S_1)$ and a locus of instantaneous centers of rotation $(C_2)$ of said second convex articulation surface $(S'_2)$ with respect to said glenoid or cotyloid articulation surface $(S_2)$, are located on opposite sides of said first convex articulation surface $(S'_1)$ thereby facilitating movement of abduction of the prosthesis.

2. The prosthesis of claim 1, wherein said first convex articulation surface $(S'_1)$ is located inside a volume (V) defined by said second convex articulation surface $(S'_2)$.

3. The prosthesis of claim 1, wherein each of said articulation surfaces is substantially in a form of a portion of a sphere.

4. The prosthesis of claim 1, wherein the first convex articulation surface ($S'_1$) and the humeral concave articulation surface ($S'_2$) are cylindrical, with rectilinear generatrix and with circular base, with their axis of symmetry substantially antero-posterior, while the second convex articulation surface and the glenoid articulation surface are substantially in a form of portions of a sphere.

5. The prosthesis of claim 1, wherein said intermediate component comprises a dish forming said second convex articulation surface, and a button within said dish and forming said first convex articulation surface.

6. The prosthesis of claim 1, wherein said humeral or femoral component includes a plate, forming the concave articulation surface which cooperatively slides with respect said first convex articulation surface and a part to be anchored in the humeral or femoral medullar cavity, and said plate being connected to said part by a linking stem.

7. The prosthesis of claim 6, wherein said plate is of non-circular shape.

8. The prosthesis of claim 7, wherein a smallest dimension of said plate is disposed parallel to a sagittal plane.

9. The prosthesis of claim 1, wherein said intermediate component is of bi-convex shape.

10. The prosthesis of claim 1, including a glenoid or cotyloid component forming said concave glenoid or cotyloid articular surface.

11. The prosthesis of claim 1, wherein a part forming said first concave articulation surface ($S'_1$) of said humeral or femoral component is provided with at least one projection (14) adapted to be engaged in a notch (34) of corresponding shape of said intermediate component.

12. The prosthesis of claim 1, wherein said intermediate component includes a washer (33) immobilized in a dish forming said second articulation surface, an inner surface of said washer being adapted to limit an amplitude of relative displacement between said humeral or femoral component and said intermediate component.

13. The prosthesis of claim 1, wherein said humeral or femoral component is in two parts and comprises an anchoring stem on which is mounted an element defining said humeral or femoral concave articulation surface ($S_1$).

* * * * *